United States Patent
Jung et al.

(10) Patent No.: US 9,340,818 B2
(45) Date of Patent: May 17, 2016

(54) DIAGNOSTIC APPARATUS AND DIAGNOSTIC METHOD USING THE SAME

(75) Inventors: Jaean Jung, Daegu (KR); Jae-Kyoung Choi, Daegu (KR); Won-Jung Kim, Daegu (KR); Tae-Hee Koo, Daegu (KR); Min-A Park, Daegu (KR)

(73) Assignee: ACCESS BIO, INC., Somerset, NJ (US)

( * ) Notice: Subject to any disclaimer, the term of this patent is extended or adjusted under 35 U.S.C. 154(b) by 213 days.

(21) Appl. No.: 13/878,337

(22) PCT Filed: Oct. 5, 2011

(86) PCT No.: PCT/KR2011/007354
§ 371 (c)(1),
(2), (4) Date: May 10, 2013

(87) PCT Pub. No.: WO2012/047009
PCT Pub. Date: Apr. 12, 2012

(65) Prior Publication Data
US 2013/0224781 A1    Aug. 29, 2013

(30) Foreign Application Priority Data
Oct. 8, 2010   (KR) .......................... 10-2010-0098081

(51) Int. Cl.
| | | |
|---|---|---|
| *G01N 33/00* | (2006.01) | |
| *C12Q 1/32* | (2006.01) | |
| *A61B 5/145* | (2006.01) | |
| *A61B 5/1455* | (2006.01) | |
| *A61B 5/1468* | (2006.01) | |
| *A61B 5/1486* | (2006.01) | |
| *G01N 27/327* | (2006.01) | |

(52) U.S. Cl.
CPC ................ *C12Q 1/32* (2013.01); *A61B 5/1468* (2013.01); *A61B 5/1486* (2013.01); *A61B 5/14542* (2013.01); *A61B 5/14551* (2013.01); *G01N 27/3274* (2013.01); *A61B 2562/0295* (2013.01); *A61B 2562/063* (2013.01)

(58) Field of Classification Search
CPC . G01N 27/3274; A61B 5/1452; A61B 5/1468
See application file for complete search history.

(56) References Cited

U.S. PATENT DOCUMENTS

| | | | |
|---|---|---|---|
| 6,844,149 | B2 | 1/2005 | Goldman |
| 7,887,750 | B2 | 2/2011 | Blatt et al. |

(Continued)

FOREIGN PATENT DOCUMENTS

| | | |
|---|---|---|
| CN | 1964789 A | 5/2007 |
| CN | 101413941 A | 4/2009 |

(Continued)

OTHER PUBLICATIONS

Extended European Search Report dated Jan. 12, 2015 issued in corresponding European Application No. 11830894.9.
(Continued)

*Primary Examiner* — Sam P Siefke
(74) *Attorney, Agent, or Firm* — Lucas & Mercanti, LLP

(57) ABSTRACT

Provided is a diagnostic apparatus. The diagnostic apparatus includes a microfluidic chip including first and second measurement parts for respectively measuring an amount of hemoglobin and an active degree of an enzyme within a blood sample. The second measurement part of the microfluidic chip analyzes the active degree of the enzyme within the blood sample using voltammetry.

16 Claims, 3 Drawing Sheets

(56) References Cited

U.S. PATENT DOCUMENTS

| | | | |
|---|---|---|---|
| 8,747,779 B2 * | 6/2014 | Sprague et al. | 422/503 |
| 2003/0003522 A1 | 1/2003 | Goldman | |
| 2004/0191124 A1 | 9/2004 | Noetzel et al. | |
| 2005/0130236 A1 | 6/2005 | Goldman | |
| 2005/0142565 A1 | 6/2005 | Samper et al. | |
| 2005/0249633 A1 | 11/2005 | Blatt et al. | |
| 2007/0099290 A1 | 5/2007 | Iida et al. | |
| 2007/0242105 A1 | 10/2007 | Srinivasan et al. | |
| 2009/0087901 A1 | 4/2009 | Noetzel et al. | |
| 2011/0091357 A1 | 4/2011 | Blatt et al. | |
| 2014/0231259 A1 | 8/2014 | Srinivasan et al. | |

FOREIGN PATENT DOCUMENTS

| | | | |
|---|---|---|---|
| CN | 101505653 A | | 8/2009 |
| EP | 0397424 A2 | | 11/1990 |
| JP | 2003-067171 A | | 3/2003 |
| JP | 2003-215122 A | | 7/2003 |
| JP | 2005164296 A | | 6/2005 |
| JP | 2007071711 A | | 3/2007 |
| JP | 2008-170351 A | | 7/2008 |
| JP | 2008-216269 A | | 9/2008 |
| JP | 2009-530639 A | | 8/2009 |
| KR | 2004-0013003 A | | 11/2004 |
| KR | 2007-0092097 A | | 9/2007 |
| WO | WO-03/001964 A2 | | 1/2003 |
| WO | WO-2005/024436 A1 | | 3/2005 |
| WO | WO-2005/116632 A2 | | 12/2005 |
| WO | WO 2010120786 A1 * | | 10/2010 |

OTHER PUBLICATIONS

International Search Report PCT/ISA/210 for International Application No. PCT/KR2011/007354 dated May 4, 2012.

* cited by examiner

DIAGNOSTIC APPARATUS AND DIAGNOSTIC METHOD USING THE SAME

TECHNICAL FIELD

The present invention disclosed herein relates to a diagnostic apparatus and a diagnostic method using the same, and more particularly, to a diagnostic apparatus which can measure an amount of hemoglobin and an active degree of an enzyme within a blood sample at the same time and a diagnostic method using the same.

BACKGROUND ART

Generally, when the amount of specific enzymes within blood is measured, the amount of enzymes is determined through naked eye or using optical methods or electrochemical methods. Among this, the electrochemical methods may be greatly influenced by various nuisance spices such as an ascorbic acid, an acetoaminophen, or/and a uric acid which exist within a blood sample and can be easily oxidized. Specifically, serious measurement errors may occur by the hematocrit to cause incorrect decision.

Typically, to reduce the influence due to the hematocrit within blood, various methods have been proposed. Examples of the various methods may include a method in which existing signal decrement is compensated using an electric signal obtained from materials within erythrocytes for deciding the hematocrit, a method in which a reagent fixed to a surface of an electrode or a reaction membrane having an integrated blood separation function is utilized using a screen printing technology, a method in which an enzyme material reacting with a material to be analyzed is manufactured into a thin film type to prevent proteins from being absorbed on a surface of an electrode, and a method in which an applying potential is applied two times to mathematically process the resultant data for correction.

Glucose-6-phosphate dehydrogenase (G6PD) performs important functions in humans biochemical reaction. The G6PD may be a portion of a pentose phosphate cycle. Also, the G6PD is known as a material having a function which minimizes oxidative attack of active oxygen affecting cells.

The G6PD exists in all cells of human. Specifically, the G6PD may exist at a high concentration in erythrocytes which serve as oxygen carriers and are exposed to the oxidative attack too much. An action system of the G6PD has high efficiency in defense ability against undesirable oxidative effects. However, when the G6PD serving as a defense mechanism against the oxidative attack is lacked, it is known to cause serious hazards by side effects due to a drug that is used as a strong oxidizer such as a quinine-base agent of antimalarial agents administered into human.

Typical methods for measuring an active degree of the G6PD use a lateral flow kit using enzyme reaction or a diagnostic kit which is based on a fluorochrome analysis of a fluid system. However, these methods need an expensive diagnostic apparatus or it is difficult to determine carrier patients by a diagnosis through visual discrimination.

DISCLOSURE OF INVENTION

Technical Problem

The present invention provides a diagnostic apparatus which measures an amount of hemoglobin within a blood sample and simultaneously measures an active degree of an enzyme within the blood sample to confirm the activity of the enzymes with respect to the amount of hemoglobin.

The present invention also provides a diagnostic method which measures an amount of hemoglobin within a blood sample and simultaneously measures an active degree of an enzyme within the blood sample to confirm the activity of the enzymes with respect to the amount of hemoglobin.

Solution to Problem

Embodiments of the present invention provide diagnostic apparatuses. The diagnostic apparatuses include a microfluidic chip including first and second measurement parts for respectively measuring an amount of hemoglobin and an active degree of an enzyme within a blood sample.

In some embodiments, the first measurement part of the microfluidic chip may measure the amount of hemoglobin within the blood sample using photometry, voltammetry, or colorimetry. The first measurement part of the microfluidic chip may be provided in plurality to measure the amount of hemoglobin within the blood sample using a plurality of measuring methods selected from the photometry, the voltammetry, or the colorimetry.

In other embodiments, the second measurement of the microfluidic chip may include an electrode and an electron transport medium. The second measurement of the microfluidic chip may measure the active degree of the enzyme within the blood sample using voltammetry. The enzyme may be glucose-6-phosphate dehydrogenase (G6PD).

In still other embodiments, the diagnostic apparatuses may further include: a loading part on which the microfluidic chip is loaded; and a socket part circuitally connected to the loading part.

In even other embodiments, the diagnostic apparatuses may further include first and second analysis parts for analyzing values respectively measured by the first and second measurement parts of the microfluidic chip.

In yet other embodiments, the diagnostic apparatuses may further include an amplifier for amplifying values measured by the first and second measurement parts of the microfluidic chip.

In further embodiments, the diagnostic apparatuses may further include an analog-digital converter for converting values measured by the first and second measurement parts of the microfluidic chip into digital signals.

In still further embodiments, the diagnostic apparatuses may further include a display part for converting values analyzed by the first and second analysis parts into images.

In even further embodiments, the diagnostic apparatuses may further include a control part for controlling the microfluidic chip, the socket part, the first and second analysis parts, and the display part.

In much further embodiments, the microfluidic chip may include: a sample inlet port for inputting the blood sample; a sample dissolution part for converting the blood sample into lysate; a passage through which the lysate is moved into the first and second measurement parts; and lines electrically connected to the first and second measurement parts, respectively.

In still much further embodiments, the sample dissolution part may constitute the first and second measurement parts, and the branched passage may be directly connected to the sample inlet port.

In even much further embodiments, the sample dissolution part may include detergent. The detergent may include soap, sulfonate, sulfate, phosphate, phosphate, alkyl glycoside, bide acid, glucamide, polyoxyethylene, monodisperse, polydisperse, or zwittergent.

In yet much further embodiments, the sample dissolution part may further include a matrix containing the detergent. When the sample dissolution part includes the matrix, the sample dissolution part may be spaced from the first and second measurement parts by the branched passage. The matrix may include a nitrocellulose membrane, a hydrophobic pad, or a hydrophilic pad.

In other embodiments of the present invention, diagnostic methods include: putting a blood sample into a microfluidic chip including first and second measurement parts for respectively measuring the amount of hemoglobin and an active degree of an enzyme within the blood sample; dissolving the blood sample to convert the blood sample into lysate; moving the lysate into the first and second measurement parts; and measuring the amount of hemoglobin and the active degree of the enzyme through the first and second measurement parts, respectively.

In some embodiments, the first measurement part of the microfluidic chip may measure the amount of hemoglobin within the blood sample using photometry, voltammetry, or colorimetry. The first measurement part of the microfluidic chip may be provided in plurality to measure the amount of hemoglobin within the blood sample using a plurality of measuring methods selected from the photometry, the voltammetry, or the colorimetry.

In other embodiments, the second measurement of the microfluidic chip may measure the active degree of the enzyme within the blood sample using voltammetry. The enzyme may be glucose-6-phosphate dehydrogenase (G6PD).

In still other embodiments, the dissolving the blood sample may use detergent. The detergent may include soap, sulfonate, sulfate, phosphate, phosphate, alkyl glycoside, bide acid, glucamide, polyoxyethylene, monodisperse, polydisperse, or zwittergent.

In even other embodiments, the diagnostic methods may further include: amplifying values measured by the first and second measurement parts of the microfluidic chip; and converting the amplified values into digital signals.

In yet other embodiments, the diagnostic methods may further include converting values measured by the first and second measurement parts of the microfluidic chip into images.

Advantageous Effects of Invention

As described above, according to the diagnostic apparatus of the present invention, the amount of hemoglobin within the blood sample and the active degree of the enzymes within the blood sample may be measured at the same time to confirm the activity of the enzymes with respect to the amount of hemoglobin. Thus, it may prevent decision with respect to the results occurring due to the hematocrit difference of the blood sample from occurring. Therefore, the diagnostic apparatus according to the present invention may quickly and accurately diagnose diseases.

Also, according to the diagnostic method of the present invention, the amount of hemoglobin within the blood sample and the active degree of the enzymes within the blood sample may be measured at the same time to confirm the activity of the enzymes with respect to the amount of hemoglobin. Thus, it may prevent decision with respect to the results occurring due to the hematocrit difference of the blood sample from occurring. Therefore, the diagnostic apparatus according to the present invention may quickly and accurately diagnose diseases.

BRIEF DESCRIPTION OF DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

BEST MODE FOR CARRYING OUT THE INVENTION

Figure 1:
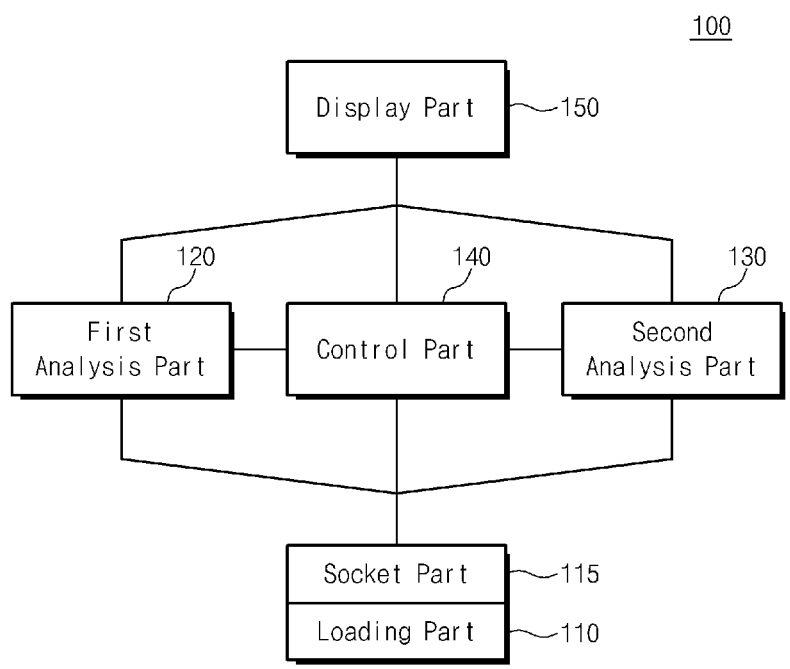
FIG. 1 is a schematic block diagram of a diagnostic apparatus according to an embodiment of the present invention.

Preferred embodiments of the present invention will be described below in more detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explain a specific exemplary embodiment while not limiting the present invention. The terms of a singular form may include plural forms unless referred to the contrary. The meaning of include, comprise, including, or comprising, specifies a property, a region, a fixed number, a step, a process, an element and/or a component but does not exclude other properties, regions, fixed numbers, steps, processes, elements and/or components. Since preferred embodiments are provided below, the order of the reference numerals given in the description is not limited thereto. Furthermore, these terms are only used to distinguish one element from another element. It will also be understood that when a layer (or film) is referred to as being on another layer or substrate, it can be directly on the other layer or substrate, or intervening layers may also be present.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. For example, a vertical etching area may have a rounded shape or a shape having a predetermined curvature. Also, areas exemplified in the drawings have general properties, and are used to illustrate a specific shape of a semiconductor package region. Thus, this should not be construed as limited to the scope of the present invention.

FIG. 1 is a schematic block diagram of a diagnostic apparatus according to an embodiment of the present invention.

Referring to FIG. 1, a diagnostic apparatus 100 includes a loading part 110, a socket part 115, first and second analysis parts 120 and 130, a control part 140, and a display part 150.

The loading part 110 provides a path for loading a microfluidic chip (see reference numeral 200 of FIG. 3) on the diagnostic apparatus 100. The socket part 115 is circuitally connected to the loading part 110 so that the diagnostic apparatus 100 reads values measured by first and second measurement parts (see reference numerals 220 and 230 of FIG. 3) of the microfluidic chip 200 and then analyzes the measured values.

The microfluidic chip 200 includes the first and second measurement parts 220 and 230. The first measurement part 220 of the microfluidic chip 200 may measure an amount of hemoglobin within a blood sample. Also, the second measurement part 230 of the microfluidic chip 200 may measure an active degree of enzymes within the blood sample. The first measurement part 220 of the microfluidic chip 200 may measure the amount of hemoglobin within the blood sample using photometry, voltammetry, or colorimetry. The second measurement part 230 of the microfluidic chip 200 may measure the active degree of the enzymes within the blood sample using the voltammetry. Also, the second measurement part 230 of the microfluidic chip 200 may measure an active degree of glucose-6-phosphate dehydrogenase (G6PD). The microfluidic chip 200 will be described again in detail with reference to FIG. 3.

The first and second analysis parts 120 and 130 analyze the values measured by the first and second measurement parts 220 and 230 of the microfluidic chip 200, respectively. That is, the first analysis part 120 analyzes the measured value with respect to the amount of hemoglobin within the blood sample measured by the first measurement part 220 of the microfluidic chip 200. Also, the second analysis part 130 analyzes the measured value with respect to the active degree of the enzymes within the blood sample measured by the second measurement part 230 of the microfluidic chip 200. The first and second analysis parts 120 and 130 may include an amplifier (see reference numeral 145 of FIG. 2) for amplifying the values measured by the first and second measurement parts 220 and 230 of the microfluidic chip 200. Also, the first and second analysis parts 120 and 130 may include an analog-digital converter (ADC: see reference numeral 147 of FIG. 2) for converting the amplified values into digital signals.

The display part 150 converts the values analyzed by the first and second analysis parts 120 and 130 into images. Since the display part 150 displays the values analyzed by the first and second analysis parts 120 and 130 as the images, the amount of hemoglobin and the active degree of the enzymes within the blood sample may be confirmed through a naked eye.

The control part 140 is electrically connected to the socket part 115, the first and second analysis parts 120 and 130, and the display part 150 to control the socket part 115, the first and second analysis parts 120 and 130, and the display part 150. That is, the microfluidic chip 200 loaded on the loading part 110 of the diagnostic apparatus 100 may be controlled also by the control part 140 through the socket part 115. Thus, the values measured by the first and second measurement parts 220 and 230 of the microfluidic chip 200 may be transmitted into the first and second analysis parts 120 and 130, and the values analyzed by the first and second analysis parts 120 and 130 may be displayed through the display part 150.

Figure 2:
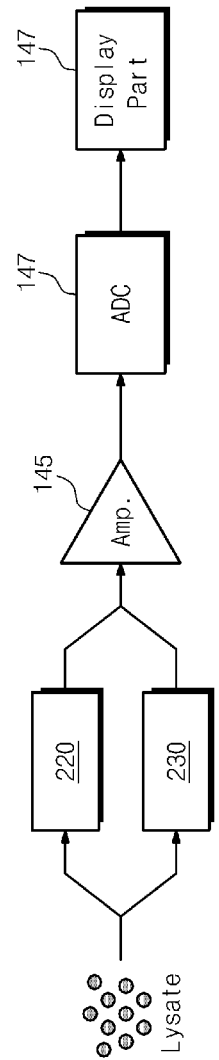
FIG. 2 is a schematic flowchart illustrating a process of measuring a fixed amount of hemoglobin and activity of enzymes within blood at the same time using a diagnostic apparatus according to an embodiment of the present invention.

FIG. 2 is a schematic flowchart illustrating a process of measuring a fixed amount of hemoglobin and activity of enzymes within blood at the same time using a diagnostic apparatus according to an embodiment of the present invention.

Referring to FIG. 2, blood samples are put into the microfluidic chip (see reference numeral 200 of FIG. 3) loaded on the diagnostic apparatus (see reference numeral 100 of FIG. 1). The blood samples put into the microfluidic chip 200 is dissolved and changed into lysate. The lysate is moved into the first and second measurement parts 220 and 230 of the microfluidic chip 200. The lysate biologically reacts within the first and second measurement parts 220 and 230 of the microfluidic chip 200, respectively.

The amount of hemoglobin within the lysate may be measured through the biological reaction occurring in the first measurement part 220 of the microfluidic chip 200. Also, the active degree of the enzymes within the lysate may be measured through the biological reaction occurring in the second measurement part 230 of the microfluidic chip 200. The biological reaction occurring in the first measurement part 220 of the microfluidic chip 200 may be measured using the photometry, the voltammetry, or the colorimetry. Here, the first measurement part 220 of the microfluidic chip 200 may be provided in plurality to measure the biological reaction using a plurality of measuring methods selected from the photometry, the voltammetry, or the colorimetry. Also, the biological reaction occurring in the second measurement part 230 of the microfluidic chip 200 may be measured using the voltammetry. The second measurement part 230 of the microfluidic chip 200 may measure the active degree of the G6PD. The microfluidic chip 200 will be described again in detail with reference to FIG. 3.

The measured values with respect to the amount of hemoglobin and the active degree of the enzymes within the lysate measured by the first and second measurement parts 220 and 230 of the microfluidic chip 200 may be amplified by the amplifier 145. The amplified values are converted into digital signals through the ADC 147. The measured values converted into the digital signals are converted into images by the display part 150. Then, the images are displayed on the display part 150 so that the measured values are confirmed through the naked eye.

Figure 3:
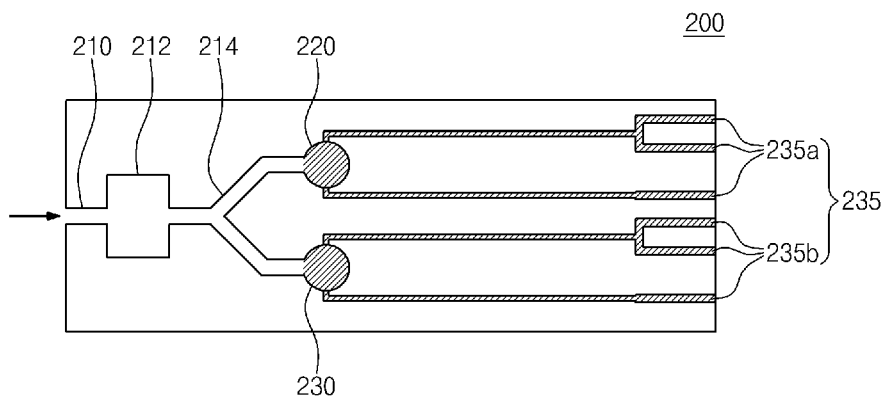
FIG. 3 is a schematic plan view of a microfluidic chip used in a diagnostic apparatus according to an embodiment of the present invention.

FIG. 3 is a schematic plan view of a microfluidic chip used in a diagnostic apparatus according to an embodiment of the present invention.

Referring to FIG. 3, a microfluidic chip 200 may perform various functions such as movement, stop, a speed variation, mixing with other fluid such as a test solution, separation, and replacement of a fluidic biological sample, i.e., a blood sample. The microfluidic chip 200 according to the present invention may include a sample inlet port 210, a sample dissolution part 212, a passage 214, first and second measurement parts 220 and 230, and lines 235.

The sample inlet port 210 may serve as a path for putting the blood sample into the microfluidic chip 210, and simultaneously, serve as a passage for transferring the put blood sample into the sample dissolution part 212. The microfluidic chip 200 according to the present invention may transfer the blood sample using a capillary force. Alternatively, the microfluidic chip 200 according to the present invention may transfer the blood sample using various methods except the capillary force.

The sample dissolution part 212 may convert the put blood sample into lysate. The sample dissolution part 212 may include detergent for converting the blood sample into the lysate. The detergent may include at least one selected from surfactant, washing, and combinations thereof. The surfactant may include at least one selected from soap, sulfonate, sulfate, phosphate, phosphate, and combinations thereof. The washing may include at least one selected from alkyl glycoside, bide acid, glucamide, polyoxyethylene, monodisperse, polydisperse, zwittergent, and combinations thereof.

The sample dissolution part 212 may further include a matrix containing the detergent. Here, the matrix may be used for a common name of materials through which liquid can pass, such as a membrane, a pulp, and a sponge. That is, the sample dissolution part 212 may include a matrix processed to contain the detergent. The matrix may include at least one selected from a nitrocellulose membrane, a hydrophobic pad, a hydrophilic pad, and combinations thereof. The matrix may not be provided according to a kind or/and concentration of the detergent contained in the sample dissolution part 212. When the matrix is not provided, the sample dissolution part 212 may include the first and second measurement parts 220 and 230. Also, the branched passage 214 may be directly connected to the sample inlet port 210.

The passage 214 may transfer the lysate into the first and second measurement parts 220 and 230. Since each of the first and second measurement parts 220 and 230 should transfer the lysate, the passage 214 may be branched in a Y-shape. The microfluidic chip 200 according to the present invention may transfer the lysate using various methods in addition to the capillary force.

The first and second measurement parts 220 and 230 may biologically react with the transferred lysate. The amount of hemoglobin within the lysate may be measured through the biological reaction occurring in the first measurement part 200. Also, an active degree of enzymes within the lysate may be measured through the biological reaction occurring in the second measurement part 230. The biological reaction occurring in the first measurement part 220 may be measured using photometry, voltammetry, or colorimetry. Although not shown, the first measurement part 220 may be provided in plurality to measure the biological reaction using a plurality of measuring methods selected from the photometry, the voltammetry, or the colorimetry. The biological reaction occurring in the second measurement part 230 may be measured using the voltammetry. The second measurement part 230 may measure an active degree of G6PD.

The lines 235 may be electrically connected to the first and second measurement parts 220 and 230, respectively. That is, the lines 235 may include lines 235a for the first measurement part 220 (hereinafter, referred to as first measurement part lines 235a) and lines 235b for the second measurement part 230 (hereinafter, referred to as second measurement part lines 235b). When the biological reaction is not measured through the voltammetry in the first measurement part 220, the first measurement part lines 235a electrically connected the first measurement part 220 may be omitted. Each of the lines 235 may have various shapes, unlike those illustrated in FIG. 3.

Figure 4:
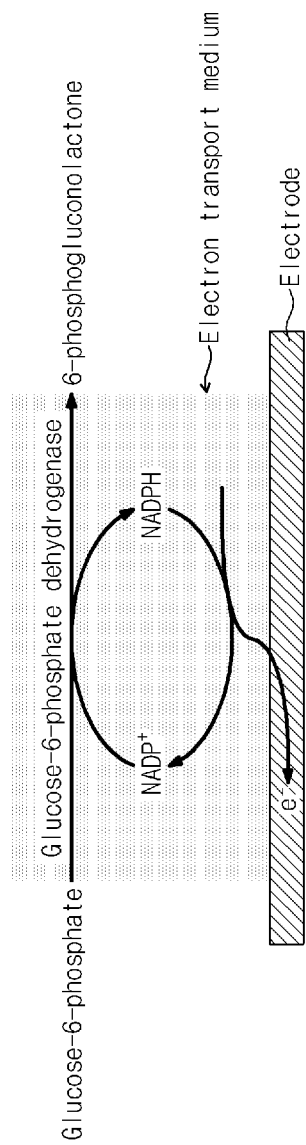
FIG. 4 is a schematic conception view illustrating a process of measuring activity of enzymes within a blood sample using a diagnostic apparatus according to an embodiment of the present invention.

Since the second measurement part 230 measures the active degree of the enzymes within the lysate using the voltammetry, the second measurement part 230 may include an electrode (see reference symbol electrode of FIG. 4) and an electron transport medium (see reference symbol electron transport medium of FIG. 4). That is, the second measurement part 230 may recognize the biological reaction through an electrochemical phenomenon due to the electrode to which a current is applied through the second measurement part lines 235b, the enzymes within the lysate, and the electron transport medium. Thus, the biological reaction occurring in the first measurement part 220 may be measured to quantify the amount of hemoglobin within the lysate, and the biological reaction occurring in the second measurement part 230 may be measured to measure the active degree of the enzymes within the lysate, thereby measuring the activity of the enzymes with respect to the amount of hemoglobin within the blood sample.

FIG. 4 is a schematic conception view illustrating a process of measuring activity of enzymes within a blood sample using a diagnostic apparatus according to an embodiment of the present invention.

Referring to FIG. 4, glucose-6-phosphate within a blood sample may cause a dehydrogenation reaction by G6PD to generate 6-phoshogluconolacton in a second measurement part of the microfluidic chip (see reference numeral 200 of FIG. 3). Also, nicotinamide adenine dinucleotide phosphate+ ($NADP^+$) and nicotinamide adenine dinucleotide phosphate H (NADPH) may be generated by the dehydrogenation reaction in the second measurement part. Electrons ($e^-$) generated when the NADPH is converted into the $NADP^+$ flow into the electrode through the electron transport medium included in the second measurement part of the microfluidic chip 200. That is, the amount of electrons ($e^-$) injected into the electrode include in the second measurement part of the microfluidic chip 200 may be varied according to an active degree of the G6PD. Thus, the amount of electrons ($e^-$) injected into the electrode include in the second measurement part of the microfluidic chip 200 may be measured to measure the active degree of the G6PD within the blood sample.

The diagnostic apparatus according to the present invention may measure the amount of hemoglobin within the blood sample and simultaneously measure the active degree of the enzymes within the blood sample to confirm the activity of the enzymes with respect to the amount of hemoglobin. Thus, it may prevent decision with respect to the results occurring due to a hematocrit difference of the blood sample from occurring. Therefore, the diagnostic apparatus according to the present invention may quickly and accurately diagnose diseases.

Also, according to the diagnostic method of the present invention, the amount of hemoglobin within the blood sample and the active degree of the enzymes within the blood sample may be measured at the same time to confirm the activity of the enzymes with respect to the amount of hemoglobin. Thus, it may prevent decision with respect to the results occurring due to the hematocrit difference of the blood sample from occurring. Therefore, the diagnostic apparatus according to the present invention may quickly and accurately diagnose diseases.

Although the preferred embodiments of the present invention will be described below in more detail with reference to the accompanying drawings, it will be understood by those skilled in the art that various changes in form and details may be made therein without departing from the spirit and scope of the invention as defined by the appended claims. Thus, it should be understood that the preferred embodiments should be considered in descriptive sense only and not for purposes of limitation.

The invention claimed is:

1. A diagnostic apparatus comprising a microfluidic chip comprising first and second measurement parts for respectively measuring an amount of hemoglobin and an active degree of an enzyme within a blood sample,
wherein the microfluidic chip comprises:
a sample inlet port for inputting the blood sample;
a sample dissolution part for converting the blood sample into lysate;
a passage through which the lysate is moved into the first and second measurement parts; and
lines electrically connected to the first and second measurement parts, respectively,
wherein
the sample dissolution part comprises detergent, and
the second measurement part of the microfluidic chip comprises an electrode and an electron transport medium.

2. The diagnostic apparatus of claim 1, wherein the first measurement part of the microfluidic chip measures the amount of hemoglobin within the blood sample using photometry or voltammetry.

3. The diagnostic apparatus of claim 2, wherein the first measurement part of the microfluidic chip is provided in plurality to measure the amount of hemoglobin within the blood sample using a plurality of measuring methods selected from the photometry, the voltammetry, or the colorimetry.

4. The diagnostic apparatus of claim 1, wherein the second measurement of the microfluidic chip measures the active degree of the enzyme within the blood sample using voltammetry.

5. The diagnostic apparatus of claim 4, wherein the enzyme is glucose-6-phosphate dehydrogenase (G6PD).

6. The diagnostic apparatus of claim 1, further comprising:
a loading part on which the microfluidic chip is loaded; and
a socket part circuitally connected to the loading part.

7. The diagnostic apparatus of claim 1, further comprising first and second analysis parts for analyzing values respectively measured by the first and second measurement parts of the microfluidic chip.

8. The diagnostic apparatus of claim 1, further comprising an amplifier for amplifying values measured by the first and second measurement parts of the microfluidic chip.

9. The diagnostic apparatus of claim 1, further comprising an analog-digital converter for converting values measured by the first and second measurement parts of the microfluidic chip into digital signals.

10. The diagnostic apparatus of claim 1, further comprising a display part for converting values analyzed by the first and second analysis parts into images.

11. The diagnostic apparatus of claim 1, further comprising a control part for controlling the microfluidic chip, the socket part, the first and second analysis parts, and the display part.

12. The diagnostic apparatus of claim 1, wherein the sample dissolution part constitutes the first and second measurement parts, and
the branched passage is directly connected to the sample inlet port.

13. The diagnostic apparatus of claim 1, wherein the detergent comprises at least one selected from soap, sulfonate, sulfate, phosphate, phosphate, alkyl glycoside, bide acid, glucamide, polyoxyethylene, monodisperse, polydisperse, zwittergent, and combinations thereof.

14. The diagnostic apparatus of claim 1, wherein the sample dissolution part further comprises a matrix containing the detergent.

15. The diagnostic apparatus of claim 14, wherein, when the sample dissolution part comprises the matrix, the sample dissolution part is spaced from the first and second measurement parts by the branched passage.

16. The diagnostic apparatus of claim 14, wherein the matrix comprises at least one selected from a nitrocellulose membrane, a hydrophobic pad, a hydrophilic pad, and combinations thereof.

* * * * *